(12) United States Patent
Duineveld et al.

(10) Patent No.: US 7,916,282 B2
(45) Date of Patent: Mar. 29, 2011

(54) SURFACE DETECTION SYSTEM FOR USE WITH A DROPLET SPRAY ORAL CLEANING DEVICE

(75) Inventors: Paulus Cornelis Duineveld, Drachten (NL); Joseph W. Grez, North Bend, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 275 days.

(21) Appl. No.: 12/303,155

(22) PCT Filed: Jun. 25, 2007

(86) PCT No.: PCT/IB2007/052456
§ 371 (c)(1),
(2), (4) Date: Dec. 2, 2008

(87) PCT Pub. No.: WO2008/001303
PCT Pub. Date: Jan. 3, 2008

(65) Prior Publication Data
US 2009/0251687 A1    Oct. 8, 2009

Related U.S. Application Data

(60) Provisional application No. 60/818,237, filed on Jun. 29, 2006.

(51) Int. Cl.
*G01N 21/00* (2006.01)
*A61C 17/00* (2006.01)

(52) U.S. Cl. ............... 356/72; 356/448; 433/80

(58) Field of Classification Search ............ 356/72, 356/448; 433/80, 89, 216; 601/162
See application file for complete search history.

(56) References Cited

U.S. PATENT DOCUMENTS

| | | | |
|---|---|---|---|
| 4,872,837 A * | 10/1989 | Issalene et al. | 433/29 |
| 5,382,163 A | 1/1995 | Putnam | |
| 5,653,591 A | 8/1997 | Loge | |
| 5,954,712 A | 9/1999 | Goodman et al. | |
| 7,163,397 B2 * | 1/2007 | Hahn et al. | 433/89 |
| 7,467,946 B2 * | 12/2008 | Rizoiu et al. | 433/29 |
| 2005/0272001 A1 | 12/2005 | Blain | |
| 2009/0017423 A1 * | 1/2009 | Gottenbos et al. | 433/216 |

FOREIGN PATENT DOCUMENTS

| | | |
|---|---|---|
| DE | 19510635 | 9/1996 |
| EP | 0933096 | 8/1999 |
| WO | 02074160 | 9/2002 |
| WO | 2005070324 A1 | 8/2005 |

* cited by examiner

Primary Examiner — L. G Lauchman

(57) ABSTRACT

The surface detection system includes a source of an optical interrogating signal (44) which accompanies a droplet spray in an oral cleaning device directed to an oral surface (46). The interrogating optical signal is reflected from the oral surface which the spray impacts and detected (48). A selected characteristic of the reflected signal, such as intensity, is indicative of the nature of the oral surface, such as either gum tissue or a tooth surface. The detected reflected signal is then processed to determine the nature of the oral reflecting surface. The processor (50) then provides a resulting output signal which can be used to either warn the user concerning the nature of the oral surface or to change the characteristics of the spray appropriately according to the surface (51).

17 Claims, 3 Drawing Sheets

SURFACE DETECTION SYSTEM FOR USE WITH A DROPLET SPRAY ORAL CLEANING DEVICE

This invention relates generally to droplet spray oral cleaning systems and more particularly concerns a system for determining when the spray is being directed to gum tissues or the teeth, so as to reduce the possibility of harm to gum tissues while otherwise maintaining sufficient power in the spray droplets to effectively clean teeth.

Droplet spray cleaning systems for cleaning teeth are in general known. In some cases, the spray is generated by forcing liquid under high pressures through a swirl nozzle. However, the resulting high pressure spray can cause harm, particularly to oral tissues, if not carefully controlled and monitored.

Other systems use a lower pressure, but effective, droplet spray system created by the use of a gas (air) stream interacting with a liquid stream to produce and accelerate a spray of droplets. In such a system, which is described in International Publication No. WO 2005070324, which owned by the assignee of the present invention and is hereby incorporated by reference.

Even in the lower pressure systems, however, the power of the spray created must still be limited because of possible potential harm to the oral tissues of the user when the spray is held in one position too long or if the velocity of the droplets is too high. When the power, i.e. the momentum, and/or velocity, of the droplets becomes too great relative to exposure time, the gum tissue or other soft tissue in the mouth can be damaged. However, the same level of power, maintained for the time which causes tissue damage, is often necessary to create effective cleaning of the teeth. In fact, it is often desirable to increase the regular power of an existing spray to increase effectiveness of the cleaning. It is important that the power of the spray be sufficient that plaque removal can be at least as good as with a more conventional electric toothbrush.

Accordingly, it is desirable that a droplet spray oral cleaning system have a capability of indicating when the spray is directed at the gums or other soft tissue instead of the teeth. Various further actions are then possible, such as by the user to move the spray away from the more delicate tissues and to position the spray so that it covers the teeth. Such a warning system would allow a high enough power level for the spray to produce effective teeth cleaning while at the same time providing protection against damage to the oral tissues.

Accordingly, the present invention is a system for detecting when a droplet spray produced by an oral cleaning device is directed toward an oral surface, comprising: a source of an interrogating signal which accompanies the droplet spray to an oral surface impacted by the spray, wherein the interrogating signal is reflected from the oral surface and wherein a selected characteristic of the reflected signal varies according to the oral surface impacted; a detector for detecting the reflected signal and a processor for identifying the oral surface impacted based on the selected characteristic of the reflected signal; and a system responsive to the processor for providing an indication to the user of the identity of the oral surface or altering the droplet spray in accordance with the identified oral FIG. 1 is a generalized diagram showing a typical liquid droplet spray oral cleaning system in which the spray location/detection system of the present invention may be used.

Figure 1:
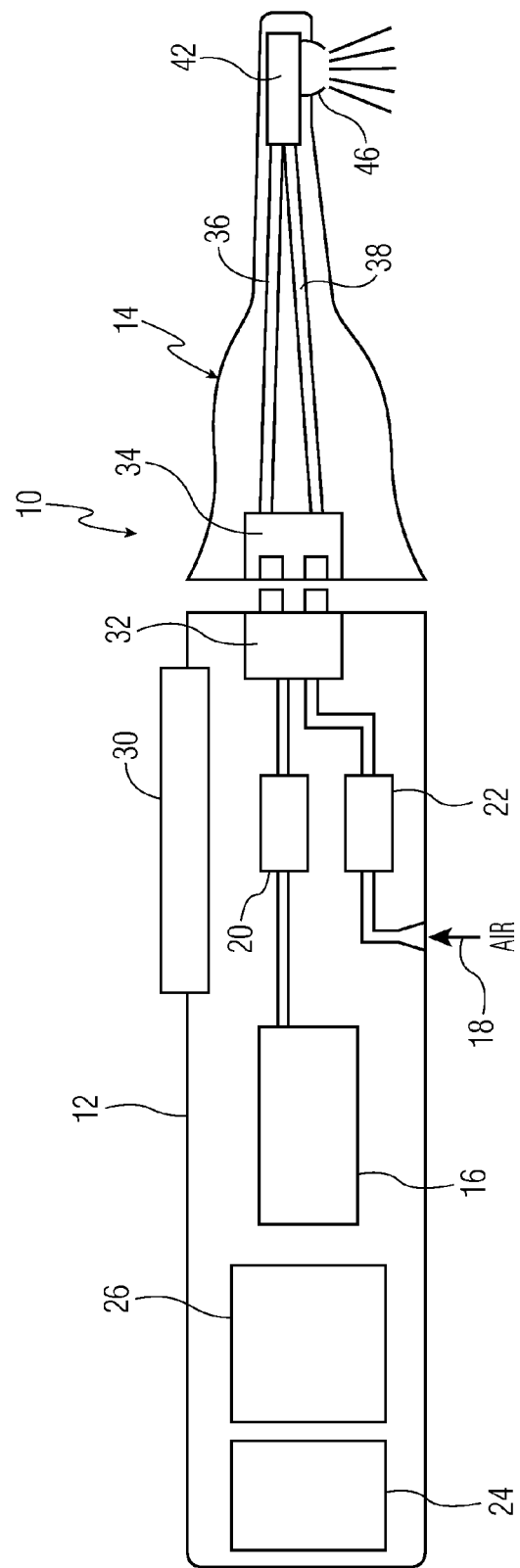

FIG. 1 shows a droplet spray oral cleaning apparatus, referred to generally at 10. The apparatus of FIG. 1 includes a handle portion 12 and a removable head portion 14. The handle includes a reservoir for liquid 16 and an air intake 18, although an internal gas reservoir, including compressed gas, can also be used. Pumps 20 and 22 are associated with the liquid reservoir and the gas intake respectively, and move the gas and liquid through associated flow lines into the head portion. A pump is not necessary for the gas line if a pressurized gas reservoir is used.

The apparatus shown has an internal power source 24, which can be batteries, for instance, while operation of the apparatus is controlled by an electronic control system 26. A user interface 30 which includes an on/off switch, provides the user with the ability to control the operation of the apparatus.

In the arrangement shown, the handle and head include, respectively, interface portions 32 and 34, which permit the head portion to be conveniently removed and replaced, although this is not necessary to the present spray location/detection system. Liquid and gas lines 36, 38 in the head portion receive liquid and gas from pumps 20 and 22, and deliver the liquid and gas to a spray generator, shown generally at 42, which includes an exit nozzle 46.

In the spray generator 42, disclosed in the '324 publication, a liquid droplet spray is created, which exits from nozzle 46 and is directed toward the user's teeth when properly positioned in the mouth by the user. The liquid droplets leave the nozzle with a sufficient velocity, above 30 meters per second, to produce effective cleaning. The droplets exit with a power, i.e. a momentum, which is effective to clean teeth, but could create damage to the oral tissues, such as the gums, if left in a position on the gums for too long of a time. As the velocity of the droplets increases, safety issues relative to soft tissue in the mouth become more significant, particularly when the average velocity of the droplets goes above 70 meters per second. The average liquid velocity is typically maintained below this critical velocity. However, for very effective cleaning it may be desirable to have the droplet velocity at or even somewhat above that value. Careful attention must be paid to potential tissue damage. As an example, for a droplet velocity of 70 meters per second, with a typical flow rate of 20 ml per minute, a spray area of 4.5 $mm^2$, a specific momentum, defined as the liquid main flow rate times the liquid average velocity divided by the spray area, of approximately 5 kpa results. With this momentum, there is a maximum exposure time of approximately 6 seconds before damage will occur to oral tissues.

In one embodiment of the present invention, a warning is provided to the user when the spray is determined to be directed at oral tissues (such as gums) instead of teeth. This warning can take various forms. In one arrangement, a warning signal is produced, specifically an audible sound, a visible indication or a vibration of the apparatus, which indicates to the user that the apparatus should be moved within the mouth, so that the spray is directed to the teeth. In another arrangement (embodiment), the power of the droplets is reduced automatically when it is recognized that the spray is going against tissue, either by decreasing the air flow rate or the liquid flow rate to the sprayhead. When the spray is recognized to be directed against the teeth, the air flow rate or liquid flow rate can then be increased. In another arrangement (embodiment), the spray can be terminated for a selected period of time when the spray is recognized to be directed to tissue surfaces.

Figure 2:
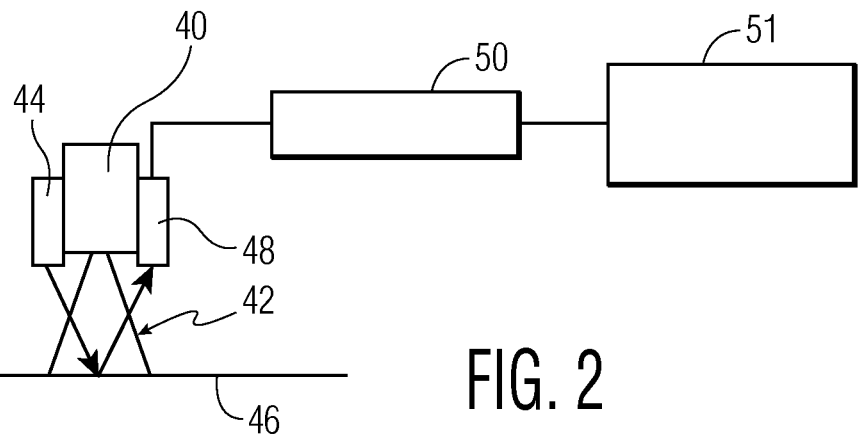
FIG. 2 is a simplified diagram showing one embodiment of an optical location system.

It should be understood that the surface detection can be done by various means, including, for example, optical, mechanical, electrical and audio. Preferably, the apparatus will operate optically. Referring now to FIG. 2, a nozzle portion of a droplet spray cleaning apparatus is shown in simple form at 40. The nozzle produces a spray of droplets 42, having a defined spray angle, which is directed toward a certain area of the mouth. In the embodiment shown, positioned on one side of the nozzle 40 is a light source 44 which directs a beam of light to the oral surface 46, which could be teeth or tissue, which surface reflects the light to a detector 48. In the arrangement shown, the light beam is directed to the center of the spray. The reflected light beam will be different from the transmitted light beam in several respects. For instance, the intensity of the reflected light will be different, and there will be a phase difference. If the two surfaces are different colors (gums/pink; teeth/white), the reflected light will indicate that, recognized by the detector 48.

The reflected light beam will then be directed from the detector to a processor 50 which will make a determination of the reflected surface. The results from the processor 50, if a tissue surface is detected, can then be directed toward a warning system, or a control system for the air flow or liquid flow lines, represented at 51, either resulting in a decrease in the action of the droplet spray, or termination thereof for a brief time, such as between a fraction of a second to a second, or until the color identification of the surface changes. If a tooth surface is detected, the spray will continue as is, although the velocity could be increased somewhat, if desired, for better cleaning.

The interrogating light signal can be a single ray, multiple rays, or a ring of light rays, which can enclose the entire area of the spray. Hence, it should be understood that a variety of arrangements can be used with an optical interrogating system using a beam or beams of light.

As indicated above, besides optical, other interrogating signals can be used, including an electrical signal which will interact differently with teeth than with tissues. The returning electrical signal will be different in one or more discernable ways than the transmitted signal. An audio signal can also be used, with again the reflected/returning signal being different than the transmitted signal, depending on the type of reflecting surface, with hard tissue (such as teeth) being more reflective than soft tissue (gums).

In some cases, when the droplet spray is continuous, the resulting liquid present on the teeth or gums can result in an equilibrium condition of a liquid layer on the teeth, which, while thin, can interfere with an interrogating signal. In order to correct this, the flow of liquid to the spray generator (sprayhead) can be periodically interrupted (such as at the pump in FIG. 1). This interruption can occur, for example, every few milliseconds, up to one second. During this interrupted time, fluid will be substantially eliminated from the teeth/tissues. Short spans of time in which the droplet spray is not reaching the oral surfaces allows the liquid film on the teeth to thin sufficiently that a good accurate detection result, differentiating the teeth from the tissues, can be achieved.

Figure 3:
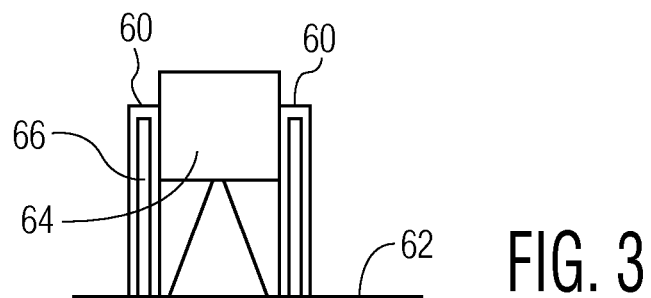
FIG. 3 is a simplified diagram showing another arrangement for a spray location system.

In another embodiment, shown in FIG. 3, the optical transmitter/detection system may be integrated into a guide member system for the sprayhead which properly positions the sprayhead relative to the oral surfaces, the guide member system insuring that the sprayhead is at a desired start-off distance from the teeth. In FIG. 3, the guide member is shown generally at 60, relative to an oral surface (either teeth or gums) 62, for a nozzle 64. The optical source and detector, integrated into the guide member, are shown by a single reference numeral at 66.

Figure 4:
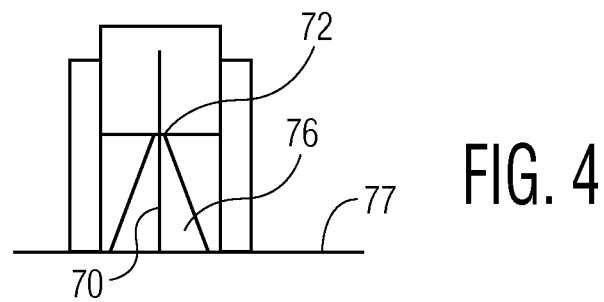
FIG. 4 is a diagram showing another spray location system.

It is also possible to have the light source positioned in the middle of the spray, with a guide member, as shown in FIG. 4, which shows a light beam 70 being directed through an orifice plate 72 along with a liquid stream 76 to an oral surface 77. The advantage of this arrangement is that the transmitted optical signal proceeds straight to the oral surface without any deviation. The light source can also be used to detect whether or not the orifice is partially or completely blocked.

Hence, various structural arrangements relative to a sprayhead nozzle can be used in the transmission and detection of an optical beam, to produce an output signal for the apparatus to prevent damage to soft tissues.

Figure 5:
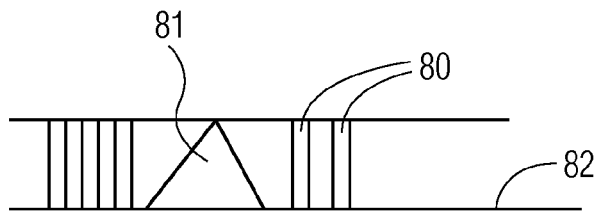
FIG. 5 is a diagram showing a further spray location system using bristles.

In another embodiment, shown in FIG. 5, a light source can be positioned in toothbrush bristles 80 which surround the spray 81 and come against an oral surface 82. In this embodiment, the bristles function as guides for the interrogating light beams. In this arrangement, the signal-to-noise ratio can be relatively high and the system will still perform well.

Typically, only one droplet spray will be generated in a sprayhead. When multiple sprays are used, there is usually at least one light source per spray, although it is possible to make an elongated light source which covers more than one spray.

The optical system described and shown herein, in the various embodiments, can also be used as a distance measurement system, and provide information concerning the distance from the sprayhead to the teeth, including providing a warning when the distance is not within a selected window. Typically, if the spray is closer than 2 mm, the acceleration of the liquid droplets may not be sufficient and cleaning will be adversely affected, while on the other hand, when the spray is too far away from the teeth, e.g. greater than 7 mm, the droplet velocity decreases sufficiently that the spray will typically not be very effective.

In such an arrangement, the user will hold the device away from contact with the teeth. The distance determination is made by the processor 50 using a phase difference calculation between the transmitted beam and the reflected beam from the oral surface. Once the distance is determined by the processor, a comparison with the desired distance is made. A warning can be given to the user, or the liquid or gas flow can be increased, with a resulting increase in initial droplet velocity, when the determined difference is greater than the desired distance window.

Figure 6A:
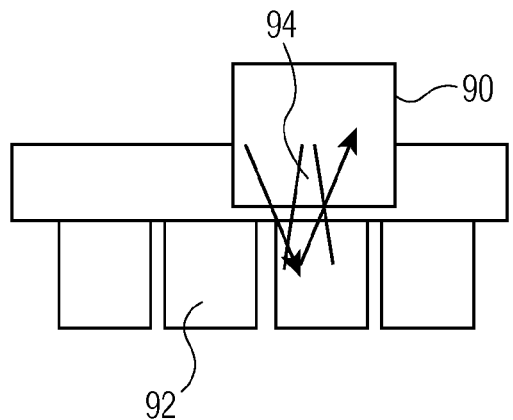
FIGS. 6A and 6B are diagrams showing the use of the system disclosed herein to find the interproximal areas of the teeth.
Figure 6B:
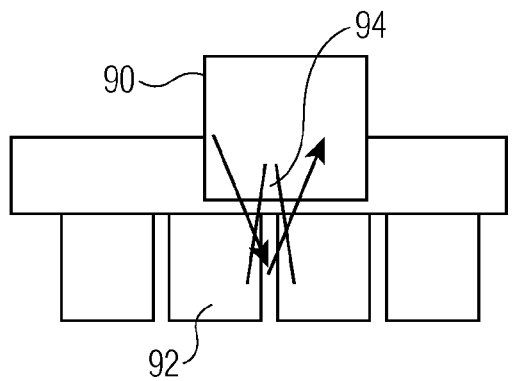

The present arrangement can also be used to determine when the spray is being directed toward the interproximal areas of the teeth, rather than the frontal regions of the teeth if it is desirable to determine that particular position. This can be detected by the system described herein, as shown in FIGS. 6A and 6B. The distance between the optical source and detector 90 (with transmitted and reflected light) relative to the teeth 92 will be shorter when the spray 94 is on the frontal region of the teeth (FIG. 6A) than the corresponding distance when the optical signal is directed to the interproximal areas of the teeth (FIG. 6B).

The system described herein can also be used with a droplet spray to detect the presence of plaque or stains on the teeth. In the arrangement where the spray droplets are created by a gas-assisted method, the landing site for the droplets on the teeth can be cleared of water or other liquid by the remaining gas stream portion of the droplet spray. If the liquid flow rate is interrupted intermittently, the teeth will be fully dry, improving the signal-to-noise ratio. Plaque can be detected directly, or with the use of a dye which adheres to the plaque, which can then be distinguished by an optical signal. The detection of plaque by this optical method can then be used to produce a warning as an indicator to guide the user to position the spray to where plaque is present, or on the other hand, the detector signal can be used to modify the spray in accordance with the thickness of the plaque.

Hence, a system has been disclosed which provides an indication of location of the spray, particularly whether the spray is being directed to the teeth or oral tissues, such as the gum tissue. A particular level of power (droplet momentum) is necessary for effective cleaning; however, the user must be careful to position the spray so that the tissues are not damaged and maintain position of the spray on the teeth. The system can also be used to determine the distance of the spray from the teeth, and also to locate, in another arrangement, the interproximal areas between the teeth.

Although a preferred embodiment has been disclosed here for purposes of illustration, it should be understood that various changes, modifications and substitutions may be incorporated in the embodiment without departing from the spirit of the invention which is defined by the claims that follow.

The invention claimed is:

1. A system for detecting when a droplet spray produced by an oral cleaning device is directed toward an oral surface, comprising:

a source of an interrogating signal (44, 66, 70, 90) which accompanies the droplet spray (42) to an oral surface (46) impacted by the spray, wherein the interrogating signal is reflected from the oral surface and wherein a selected characteristic of the reflected signal varies according to the oral surface impacted;

a detector (48) for detecting the reflected signal and a processor (50) for identifying the oral surface impacted based on the selected characteristic of the reflected signal; and a system (51) responsive to the processor for providing an indication to the user of the identity of the oral surface or altering the droplet spray in accordance with the identified oral surface.

2. The system of claim 1, wherein the interrogating signal and the reflected signal are optical.

3. The system of claim 2, wherein the selected characteristic of the reflected signal is the intensity of the optical signal, distinguishing the oral surface as either gum tissue or teeth.

4. The system of claim 1, wherein the selected characteristic of the reflected signal is the distance between a spray-head source of droplet spray and the oral surface.

5. The system of claim 1, wherein the interrogating signal is a single light ray.

6. The system of claim 1, wherein the interrogating signal comprises a plurality of light rays.

7. The system of claim 1, wherein the interrogating signal comprises a ring of light rays, substantially surrounding the droplet spray.

8. The system of claim 2, wherein the source of the interrogating signal and the detector are located in substantially the same position.

9. The system of claim 2, wherein the droplet spray is interrupted periodically for specified periods of time, and wherein the detecting system operates during those specified times.

10. The system of claim 2, wherein the oral cleaning device includes bristles, and wherein the interrogating optical signal is directed to the oral surface through the individual bristles (80).

11. The system of claim 2, wherein the oral surface is either a frontal portion of teeth or an interproximal area between two adjacent teeth.

12. The system of claim 2, wherein the oral surface is either a tooth surface or a gum tissue.

13. The system of claim 1, wherein the reflected signal provides an indication of the presence of, or lack thereof, of plaque on the teeth surface.

14. The system of claim 1, wherein the interrogating signal is an audio signal.

15. A system for detecting when a droplet spray produced by an oral cleaning device is directed toward an oral surface, comprising:

a source of a transmitted signal which accompanies the droplet spray to an oral surface impacted by the spray and then returns from the oral surface, wherein a selected characteristic of the returning signal varies according to the oral surface impacted;

a detector for detecting the returning signal and a processor for identifying the oral surface impacted based on the selected characteristic of the returning signal; and a system responsive to the processor for providing an indication to the user of the identity of the oral surface or altering the droplet spray in accordance with the identified oral surface.

16. The system of claim 15, wherein the transmitted and returning signals are optical signals.

17. The system of claim 15, wherein the transmitted and returning signals are electrical signals.

* * * * *